(12) United States Patent
Nemoto

(10) Patent No.: US 9,031,639 B2
(45) Date of Patent: May 12, 2015

(54) CHEMICAL LIQUID INJECTOR AND CT APPARATUS

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 0 days.

(21) Appl. No.: 13/643,782

(22) PCT Filed: Apr. 26, 2011

(86) PCT No.: PCT/JP2011/060158
§ 371 (c)(1),
(2), (4) Date: Oct. 26, 2012

(87) PCT Pub. No.: WO2011/136218
PCT Pub. Date: Nov. 3, 2011

(65) Prior Publication Data
US 2013/0041257 A1    Feb. 14, 2013

(30) Foreign Application Priority Data

Apr. 27, 2010  (JP) ................. 2010-101624

(51) Int. Cl.
*A61B 6/00* (2006.01)
*A61M 5/145* (2006.01)
(Continued)

(52) U.S. Cl.
CPC ............. *A61M 5/1456* (2013.01); *A61M 5/007* (2013.01); *A61M 5/14546* (2013.01);
(Continued)

(58) Field of Classification Search
USPC ................... 600/407, 431, 432; 378/8, 20, 95
See application file for complete search history.

(56) References Cited

U.S. PATENT DOCUMENTS

| | | | |
|---|---|---|---|
| 6,643,537 B1 | 11/2003 | Zatezalo et al. | |
| 7,706,498 B2 * | 4/2010 | Imai | 378/8 |
| 2006/0184122 A1 | 8/2006 | Nemoto | |
| 2006/0224066 A1 | 10/2006 | Niethammer | |
| 2007/0213662 A1 | 9/2007 | Kalafut et al. | |

(Continued)

FOREIGN PATENT DOCUMENTS

| | | |
|---|---|---|
| JP | A-2003-505211 | 2/2003 |
| JP | A-2007-518504 | 7/2007 |
| JP | A-2007-275360 | 10/2007 |

(Continued)

OTHER PUBLICATIONS

International Preliminary Report on Patentability, issued on Dec. 10, 2012 for International Application No. PCT/JP2011/060158.

*Primary Examiner* — Unsu Jung
*Assistant Examiner* — Joel Lamprecht
(74) *Attorney, Agent, or Firm* — Knobbe Martens Olson & Bear LLP

(57) ABSTRACT

Chemical liquid injector 100 includes two piston driving mechanisms 130 each moving a piston of a syringe forward, main injection condition determining section 171 determining injection conditions for a chemical liquid in main injection, test injection condition determining section 172 determining injection conditions for the chemical liquid in test injection performed prior to the main injection to inject a smaller injection amount of the chemical liquid than that in the main injection, and control section 161 creating an injection protocol in accordance with the injection conditions determined by test injection condition determining section 171 and main injection condition determining section 172 such that the chemical liquid is injected in a series of operations in which the test injection is performed, then a preset injection suspension time is present, and subsequently the main injection is performed, and further controlling operation of piston driving mechanisms 130 in accordance with the injection protocol.

10 Claims, 8 Drawing Sheets

(51) Int. Cl.
*A61M 5/00* (2006.01)
*A61M 5/172* (2006.01)
*A61M 5/168* (2006.01)
*A61M 5/142* (2006.01)
*A61M 5/19* (2006.01)
*A61B 6/03* (2006.01)

(52) U.S. Cl.
CPC .......... *A61M 5/16827* (2013.01); *A61M 5/172*
(2013.01); *A61M 2005/14208* (2013.01); *A61M*
*2205/502* (2013.01); *A61M 5/19* (2013.01);
*A61B 6/03* (2013.01); *A61B 6/481* (2013.01);
*A61B 6/4494* (2013.01); *A61B 6/507* (2013.01)

(56) References Cited

U.S. PATENT DOCUMENTS

2007/0282263 A1 12/2007 Kalafut et al.
2008/0253505 A1 10/2008 Imai

FOREIGN PATENT DOCUMENTS

| JP | A-2008-521506 | 6/2008 |
|----|---------------|--------|
| JP | A-2008-259679 | 10/2008 |
| JP | A-2009-039330 | 2/2009 |
| WO | W01/08730 A1 | 2/2001 |
| WO | WO 2005/007220 A1 | 1/2005 |
| WO | WO 2005/070294 A1 | 8/2005 |
| WO | WO 2006/058280 A2 | 6/2006 |

\* cited by examiner

CHEMICAL LIQUID INJECTOR AND CT APPARATUS

This application is the U.S. National Phase under 35 U.S.C. §371 of International Application No. PCT/JP2011/060158, filed Apr. 26, 2011, designating the U.S., and published in Japanese as WO2011/136218 on Nov. 3, 2011, which claims priority to Japanese Patent Application No. 2010-101624, filed Apr. 27, 2010, the entire content of which is incorporated herein by reference.

TECHNICAL FIELD

The present invention relates to a chemical liquid injector which injects a chemical liquid such as a contrast medium into a patient in order to obtain CT images of the patient, and a CT apparatus used in combination with the chemical liquid injector to obtain CT images of the patient.

BACKGROUND ART

Currently employed medical imaging diagnostic apparatuses include CT (Computed Tomography) scanners, MRI (Magnetic Resonance Imaging) apparatuses, PET (Positron Emission Tomography) apparatuses, angiography apparatuses, and MRA (MR Angiography) apparatuses and the like. In using the abovementioned apparatuses to obtain diagnostic images of a patient, a chemical liquid such as a contrast medium or physiological saline is often injected into the patient.

Typically, the injection of the chemical liquid into the patient is automatically performed by using a chemical liquid injector. The chemical liquid injector has an injection head on which a syringe is removably mounted, and an injection control unit controlling the operation of the injection head. The syringe has a cylinder and a piston inserted into the cylinder to be movable forward and rearward. The chemical liquid is filled into the cylinder.

The injection head has a syringe fixing mechanism removably fixing the syringe and a piston driving mechanism moving the piston while the cylinder is fixed to the injection head. An injection needle or a catheter is connected to the leading end of the cylinder through an extension tube, the injection needle or the catheter is placed or inserted into a blood vessel of the patient, and then the piston is pushed into the cylinder by the piston driving mechanism to allow the injection of the chemical liquid filled in the syringe into the patient.

The obtaining of CT images using the contrast medium is desirably performed at a timing when the contrast medium reaches a region for imaging after the contrast medium is injected and flows with the bloodstream of the patient. Representative methods of determining the imaging timing include a test injection method and a bolus tracking method.

The test injection method involves injecting small amounts of contrast medium and physiological saline prior to main scan to perform imaging of the same section as in the main scan, checking the time for the contrast medium to reach a region of interest, and predicting a contrast medium reaching time in the main scan to set the imaging timing (see Patent Document 1).

The bolus tracking method involves monitoring real-time changes in CT value in an appropriate region after the injection of the contrast medium with pre-scan at an X-ray dose lower than in main scan and starting the main scan when the CT value exceeds a predetermined threshold value (see Patent Document 2).

PRIOR ART REFERENCES

Patent Documents

Patent Document 1: Patent Application Laid-Open No. 2008-259679
Patent Document 2: Patent Application Laid-Open No. 2007-275360

SUMMARY OF THE INVENTION

Problems to be Solved by the Invention

The bolus tracking method and the test injection method, however, have the following problems from the viewpoint of the injection of the contrast medium.

Since the bolus tracking method involves the continuous injection of the contrast medium in order to monitor the manner of increase in CT value, the total injection amount of the contrast medium is increased. Since the test injection method involves the monitoring of the manner of increase in CT value through the injection of the small amount of the contrast medium, the total injection amount of the contrast medium can be reduced as compared with the bolus tracking method. In the test injection method, however, the test injection for the monitoring scan is performed besides the main injection for the main scan, and input of data for determining the conditions of each injection is individually performed. This requires that the input operation of data for determining the injection conditions should be performed for each of the test injection and the main injection so the test throughput is low. In addition, when a time interval is present between the test injection and the main injection, the heart rate of the patient may be changed during the interval to change the bloodstream of the patient. As a result, the contrast medium reaching time predicted in advance may not correspond to the actual reaching time in the main scan, so that the appropriate visualization effect may not be provided.

It is an object of the present invention to provide a chemical liquid injector and a CT apparatus which are capable of performing a test more easily with a higher throughput while the use amount of a chemical liquid is reduced.

Means for Solving the Problems

The present invention provides a chemical liquid injector on which at least one syringe having a cylinder and a piston is mounted, the chemical liquid injector injecting a chemical liquid in the syringe by moving the piston of the mounted syringe forward, including:

at least one piston driving mechanism driven to move the piston of the mounted syringe forward;

a main injection condition determining section determining an injection condition for the chemical liquid in main injection;

a test injection condition determining section determining an injection condition for the chemical liquid in test injection performed prior to the main injection, a smaller injection amount of the chemical liquid being injected in the test injection than an injection amount in the main injection; and a control section creating an injection protocol in accordance with the injection conditions determined by the test injection condition determining section and the main injection condition determining section such that the chemical liquid is injected in a series of operations in which the test injection is performed, then a preset injection suspension time is present, and subsequently the main injection is performed, and the control section further controls operation of the piston driving mechanism in accordance with the injection protocol.

In the chemical liquid injector according to the present invention, a contrast medium can be used as the chemical liquid. In this case, the syringe injecting a contrast medium as the chemical liquid is mounted in the chemical liquid injector, the main injection condition determining section has a first chemical liquid injection amount calculating section calculating an injection amount of the contrast medium in the main injection based on a weight of a patient to be injected with the contrast medium, and a first chemical liquid injection rate calculating section calculating an injection rate of the contrast medium in the main injection from the injection amount of the contrast medium calculated by the first chemical liquid injection amount calculating section and a preset injection time, and the test injection condition determining section can have a first chemical liquid injection amount calculating section calculating an injection amount of the contrast medium in the test injection from the injection rate calculated by the first chemical liquid injection rate determining section and a preset injection time.

Preferably, the syringe injecting physiological saline as the chemical liquid is further mounted, the chemical liquid injector further includes two piston driving mechanisms driven individually in association with the syringe injecting the contrast medium and the syringe injecting the physiological saline, the main injection condition determining section further includes a second chemical liquid injection amount calculating section calculating an injection amount of the physiological saline in the main injection from the injection rate calculated by the first chemical liquid injection rate calculating section and a preset injection time, the test injection condition determining section further includes a second chemical liquid injection amount calculating section calculating an injection amount of the physiological saline in the test injection from the injection rate calculated by the first chemical liquid injection rate calculating section of the main injection condition determining section and a preset injection time, and the control section controls operation of the two piston driving mechanisms such that the physiological saline is injected immediately after the injection of the contrast medium in accordance with the injection conditions determined by the test injection condition determining section and the main injection condition determining section in the test injection and the main injection.

According to another aspect of the present invention, the chemical liquid injector further includes a display device, and the control section displays the injection protocol created in accordance with the injection conditions determined by the test injection condition determining section and the main injection condition determining section in one screen on the display device.

The present invention also provides a CT apparatus used with the chemical liquid injector on which the syringe injecting the contrast medium as the chemical liquid is mounted, to obtain a CT image of the patient, including:

an imaging unit applying an X ray to the patient and collecting data of projection of the X ray transmitted through the patient; and an imaging control unit controlling operation of the imaging unit, reconstructing the data of projection of the X ray collected by the imaging unit to produce CT image data, and measuring a CT value from the produced CT image data, wherein the imaging control unit monitors the CT value through bolus tracking, and causes the imaging unit to perform a main scan after a preset scan suspension time by using a point immediately after the CT value passes a peak value as a trigger.

Effect of the Invention

According to the present invention, the chemical liquid injector is configured such that the test injection and the main injection are performed in the series of operations including the injection suspension time interposed therebetween. The CT apparatus is used with the chemical liquid injector to perform the main scan after the scan suspension time by using the point immediately after the CT value passes the peak as the trigger. This can reduce the injection amount of the chemical liquid, achieve the imaging in an appropriate timing, and perform the test more conveniently with a higher throughput.

EMBODIMENTS FOR CARRYING OUT THE INVENTION

Figure 1:
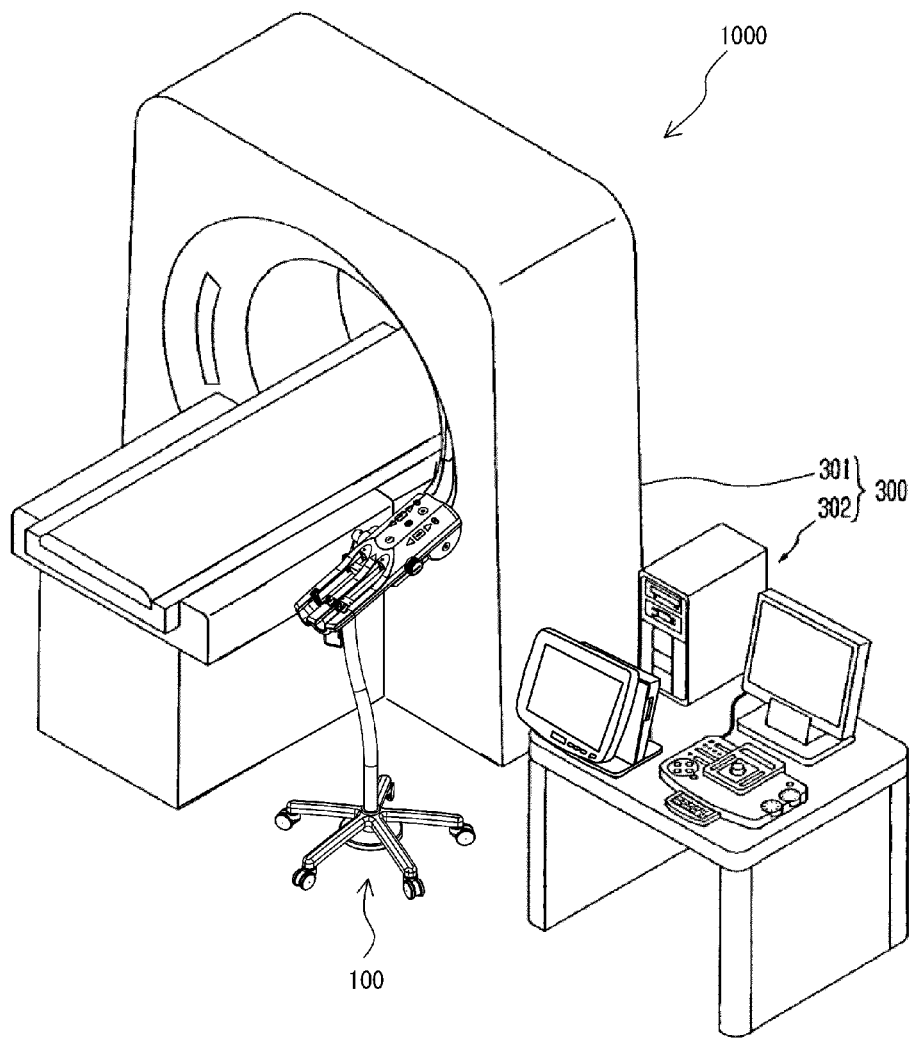
FIG. 1 A perspective view of an X-ray CT system according to an embodiment of the present invention.

Referring to FIG. 1, X-ray CT system 1000 according to an embodiment of the present invention is shown which has X-ray CT apparatus 300 serving as an imaging diagnostic apparatus and a chemical liquid injection system. The chemical liquid injection system has chemical liquid injector 100 and syringe assembly 200 (see FIG. 3) mounted on chemical liquid injector 100. X-ray CT apparatus 300 has imaging unit 301 performing an imaging operation and imaging control unit 302 controlling the operation of imaging unit 301, and units 301 and 302 are connected through a communication network.

Figure 2:
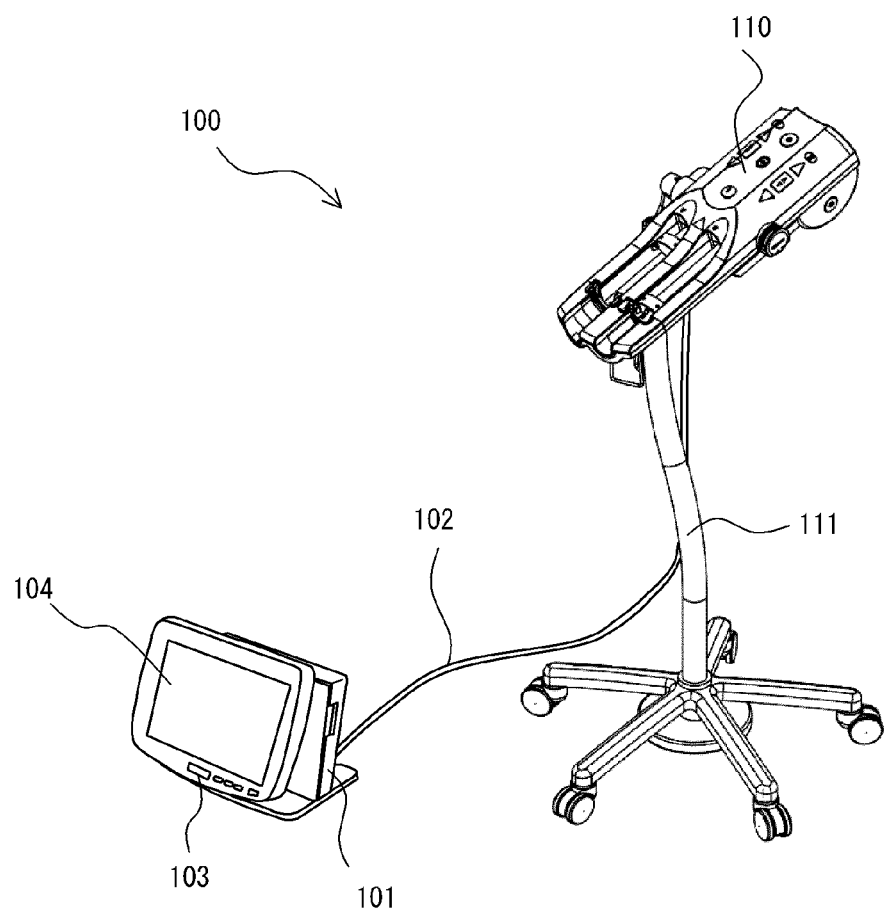
FIG. 2 A perspective view of a chemical liquid injector shown in FIG. 1.

For example as shown in FIG. 2, chemical liquid injector 100 has injection head 110 attached pivotally to the top of stand 111 and injection control unit 101 connected electrically to injection head 110 through cable 102. Injection control unit 101 has main operation panel 103 and touch panel 104 serving as both display means and input means. Injection control unit 101 may also include, for example, a hand unit (not shown) serving as auxiliary input unit connected electrically to the body of injection control unit 101 through a cable, not shown.

Figure 3:
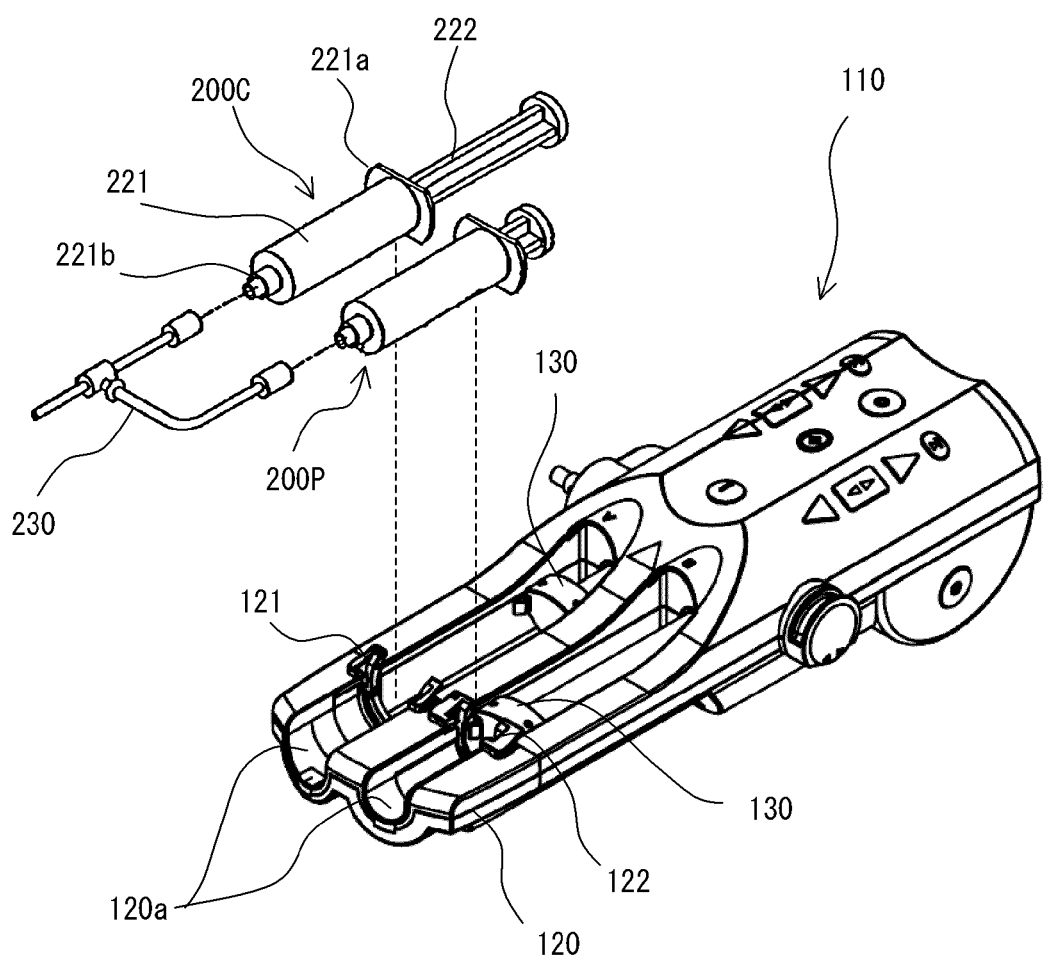
FIG. 3 A perspective view showing an injection head shown in FIG. 2 together with a syringe to be mounted thereon.

As shown in FIG. 3, two syringes 200C and 200P are removably mounted in parallel on injection head 110. Each of syringes 200C and 200P has cylinder 221 having cylinder flange 221a formed at the trailing end and nozzle portion 221b formed at the leading end, and piston 222 inserted into cylinder 221 to be movable forward and rearward.

Piston 222 is moved forward toward the leading end of cylinder 221 to push a chemical liquid filled therein out of syringe 220 through nozzle portion 221b. Nozzle portions 221b of syringes 200C and 200P are coupled to two trailing ends of extension tube 230 having the leading end connected to an injection needle or a catheter and branched into two at a point between the leading and trailing ends. The injection needle or the catheter can be placed or inserted into a blood vessel of a patient to inject the chemical liquid filled in each of syringes 200C and 200P into the patient. Examples of the chemical liquid filled in syringes 200C and 200P include a contrast medium and physiological saline. For example, one syringe 200C may be filled with the contrast medium and the other syringe 200P may be filled with the physiological saline.

Syringe receiver 120 is provided at the leading end of injection head 110 on which two syringes 200C and 200P are placed. Syringe receiver 120 has two concave portions 120a formed to receive the outer peripheral faces of cylinders 221. Syringe adapters 121 and 122 holding cylinder flanges 221a of syringes 200C and 200P are removably mounted on syringe receiver 120.

Syringes 200C and 200P placed on syringe receiver 120 are mounted on injection head 110 such that cylinder 221 is located within concave portion 121 with nozzle portion 221b facing toward the leading end and cylinder flange 221a held therein. However, syringes 200C and 200P have various sizes and/or shapes, and it is difficult to hold cylinder flanges 221a of all of syringes 200C and 200P on a common holding structure. To address this, in the present embodiment, a plurality of types of syringe adapters 121 and 122 each having a holding structure suitable for holding associated cylinder flange 221a and removably mounted on syringe receiver 120 are prepared for the respective shapes of syringes 200C and 200P to be mounted, and syringe adapters 121 and 122 are replaced for use as required to fit the types of syringes 200C and 200P, so that the various sizes and/or syringes 200C and 200P can be mounted on injection head 110.

Injection head 110 is provided with two piston driving mechanisms 130 independently driven to move pistons 222 of mounted syringes 200C and 200P forward/rearward individually or simultaneously, at positions on which syringes 200C and 200P are mounted.

Piston driving mechanism 130 has a driving motor (not shown), a motion transforming mechanism (not shown) transforming a rotational output from the driving motor into a linear motion, and a piston holding mechanism (not shown) coupled to the motion transforming mechanism to hold the trailing end of piston 222 to be freely engaged or disengaged in order to move piston 222 forward and rearward. Since a known mechanism typically used in the chemical liquid injector can be used as piston driving mechanism 130, detailed description thereof is omitted.

FIG. 3 shows a block diagram of the principal electrical configuration of the X-ray CT system according to the present embodiment. Each of the blocks shown in FIG. 5 exists as at least some or a combination of at least some of the components described in FIG. 1 to FIG. 3, and may be formed of hardware or may be formed of a logical circuit.

Figure 4:
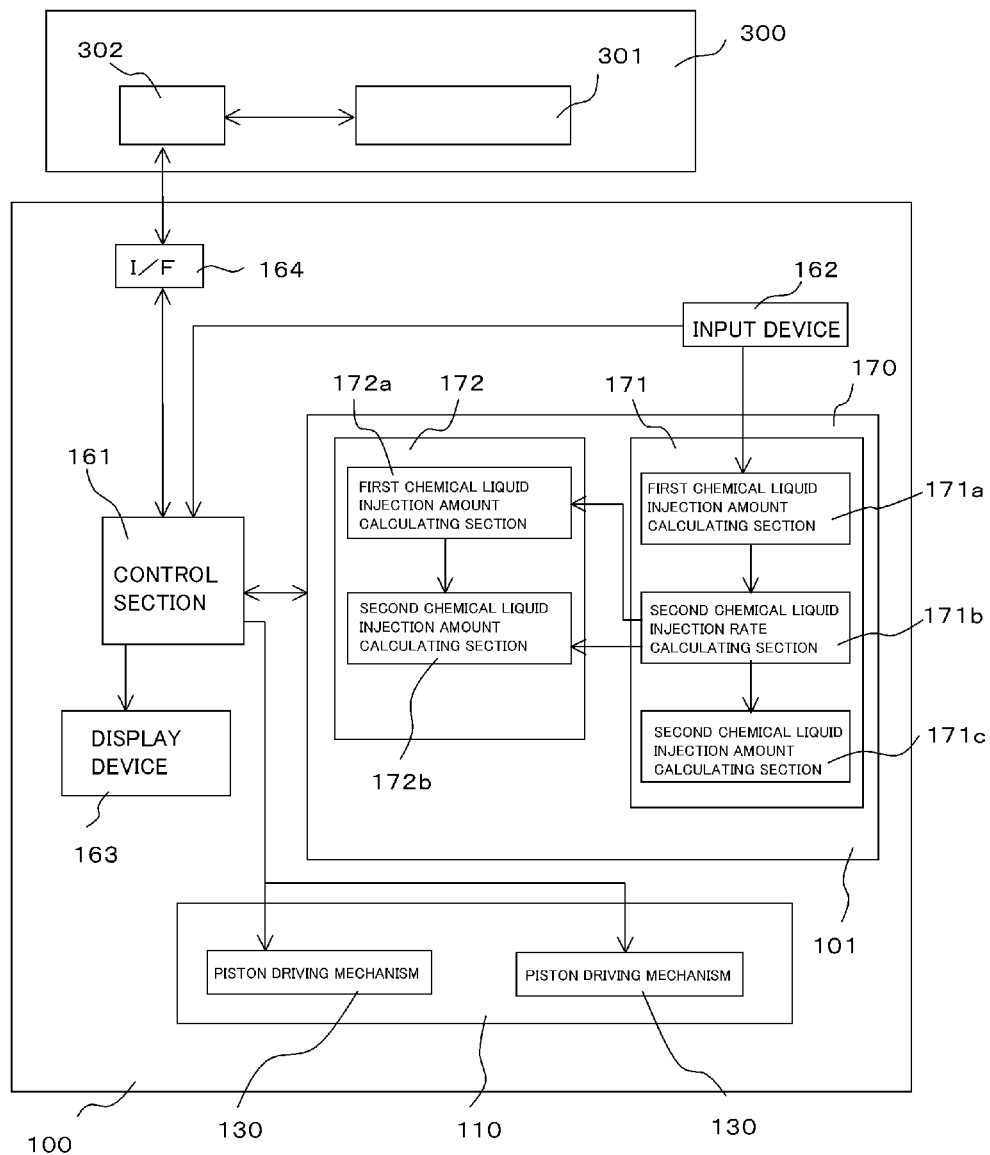
FIG. 4 A block diagram of the X-ray CT system shown in FIG. 1 represented by the functions.

As shown in FIG. 4, injection control unit 101 has control section 161, input device 162, display device 163, interface (I/F) 164, and injection condition determining section 170.

Chemical liquid injector 100 has two modes, a standard mode and a test injection association mode, as injection modes for the chemical liquid. In the standard mode, only the main injection is performed in which the chemical liquid is injected into a patient in order to obtain CT images for the purpose of diagnosis. In the test injection association mode, the main injection and test injection prior to the main injection are performed in a series of operations with a time interval interposed therebetween, and the test injection includes injection of a smaller amount of the chemical liquid than the injection amount in the main injection. The test injection is performed in order to know the manner of increase in CT value over time due to the injection of the chemical liquid.

Input device 162 corresponds to main operation panel 103 and touch panel 104 shown in FIG. 2 and receives input of various settings for chemical liquid injector 100 by an operator, data required to determine the injection conditions for the chemical liquid and the like. Display section 163 corresponds to touch panel 104 shown in FIG. 2 and displays a screen showing the operational state of chemical liquid injector 100, a screen for data input and the like. As described above, in the present embodiment, touch panel 104 has both the function as part of input section 162 and the function of display section 163.

Injection condition determining section 170 determines the injection conditions for the chemical liquid such as the injection amount and the injection rate of the chemical liquid based on the data input from input section 162 and the like. Control section 161 controls the overall operation of chemical liquid injector 100 including display of required information on display section 163 based on the input from input section 162 and control of the operation of piston driving mechanism 130 in accordance with the injection conditions for the chemical liquid determined by injection condition determining section 170 and a predetermined procedure.

An operation start signal for piston driving mechanism 130 issued by control section 161, some of the injection conditions for the chemical liquid and the like are transmitted to X-ray CT apparatus 300 through interface 164. This can associate chemical liquid injector 100 with X-ray CT apparatus 300.

Injection condition determining section 170 has main injection condition determining section 171 determining the injection amount and the injection rate of the chemical liquid in the main injection and test injection condition determining section 172 determining the injection amount of the chemical liquid in the test injection performed prior to the main injection.

Main injection condition determining section 172 has first chemical liquid injection amount calculating section 171a, first chemical liquid injection rate calculating section 171b, and second chemical liquid injection amount calculating section 171c. Of two types of chemical liquid injected by chemical liquid injector 100, a first chemical liquid refers to a chemical liquid injected first in each of the test injection and the main injection to create the image effect, and specifically refers to the contrast medium. A second chemical liquid refers to a chemical liquid injected after the first chemical liquid to chase the first chemical liquid or mix with the first chemical liquid to dilute the first chemical liquid in some cases, and specifically refers to the physiological saline. The following description is made assuming that the first chemical liquid and the second chemical liquid are the contrast medium and the physiological saline, respectively.

First chemical liquid injection amount calculating section 171a calculates the injection amount of the chemical liquid in the main injection by using at least part of the data input from input section 162. In the main injection, the injection amount (mL) of the chemical liquid is calculated in a predetermined relation including the weight (kg) of the patient, for example a calculation expression involving multiplication by a predetermined proportional coefficient. The proportional coefficient can be determined on the basis of an iodine amount (mgI/kg) required per kilogram of the patient weight and an iodine concentration (mgI/mL) of the chemical liquid. For example, assuming that the weight of the patient is represented by W (kg), the required iodine amount is represented by I (mgI/kg), and the iodine concentration is represented by C (mgI/mL), the injection amount of the chemical liquid can be calculated with the following formula (1):

Injection amount of contrast medium (mL)=$W$(kg)×$I$(mgI/kg)/$C$(mgI/mL)     [Formula 1]

Alternatively, assuming that the iodine amount required per unit weight and per unit time is represented by I' (mgI/kg/sec), and the injection time of the chemical liquid is represented by T (sec), the injection amount of the chemical liquid can be calculated with the following formula (2):

Injection amount of contrast medium (mL)=$W$(kg)×$I'$(mgI/kg/sec)/$C$(mgI/mL)×$T$(sec)     [Formula 2]

To calculate the injection amount of the chemical liquid in the main injection, the weight of the patient, the required iodine amount, and the iodine concentration are input from input device 162, and the input data is used to calculate the injection amount of the chemical liquid in the main injection by first chemical liquid injection amount calculating section 171a. Since the required iodine amount and the iodine concentration often have fixed values, I/C may be set to, for example, 0.8 in the above expressions to omit the input of the required iodine amount and the iodine concentration. Alternatively, the values of the required iodine amount and the iodine concentration may be preset as default values in injection condition determining section 146, and these values may be changed as required through an operation on input device 162. Similarly to the abovementioned case, when the values of the required iodine amount and the iodine concentration are not changed from the values set as the defaults, only the weight of the patient is required as the data input to calculate the injection amount of the chemical liquid in the main injection.

First chemical liquid injection rate calculating section 171b calculates the injection rate of the chemical liquid in the main injection by dividing the injection amount calculated by first chemical liquid injection amount calculating section 171a by the injection time. Although the injection time of the chemical liquid in the main injection may be input by the operator through input device 162, the injection time does not significantly vary depending on the other injection conditions and is often set to a time period equal to or slightly longer than an imaging time in CT apparatus 300, so that a predetermined time may be preset, for example by setting 12 seconds for the injection time of the chemical liquid when the imaging time is 10 seconds. Alternatively, a predetermined value may be set as a default value, and the operator may change the value as required. When an extended time is set, the chemical liquid is continuously injected during the extended time with the injection rate maintained, and thus the injection amount of the chemical liquid is increased in accordance with the length of the extended time.

In the main injection, the physiological saline is injected immediately after the injection of the chemical liquid in order to chase the injected chemical liquid. The injection rate of the physiological saline in the main injection is set to the same injection rate as that of the chemical liquid. The injection time of the physiological saline in the main injection can be preset to a predetermined time, for example 7 seconds, similarly to the injection time of the chemical liquid. Second chemical liquid injection amount calculating section 171c calculates the injection amount of the physiological saline in the main injection by multiplying the injection rate of the chemical liquid by the preset predetermined injection time. A predetermined value may be set as a default value for the injection time of the physiological saline, and the operator may change the value as required.

Test injection condition determining section 172 has first chemical liquid injection amount calculating section 172a and second chemical liquid injection amount calculating section 172b. Since the test injection only requires the injection of an amount of contrast medium sufficient for showing the manner of increase in CT value due to the injection of the chemical liquid, a smaller amount of chemical liquid than in the main injection may be injected. To calculate the injection amount of the chemical liquid, the injection rate and the injection time of the chemical liquid are supplied as data to first chemical liquid injection amount calculating section 172a. The injection rate of the chemical liquid in the test injection is set to the same as the injection rate of the chemical liquid in the main injection calculated by first chemical liquid injection rate calculating section 171b in order to provide the equal manners of increase in CT value due to the injection of the chemical liquid in the main injection and the test injection. For the injection time of the chemical liquid, the operator may input an appropriate value, or a predetermined time shorter than the injection time of the chemical liquid in the main injection, for example 2 seconds, may be preset. First chemical liquid injection amount calculating section 172a calculates the injection amount of the chemical liquid in the test injection from the injection rate and the injection time obtained as described above. For the injection time of the contrast medium in the test injection, a predetermined value may be set as a default value, and the operator may change the value as required.

In the test injection, the physiological saline is also injected immediately after the injection of the chemical liquid in order to push the injected chemical liquid. This allows the manner of increase in CT value to be shown with a smaller amount of chemical liquid. Second chemical liquid injection amount calculating section 172b calculates the injection amount of the physiological saline in the test injection. To calculate the injection amount of the physiological saline, the injection rate and the injection time of the physiological saline are input as data to second chemical liquid injection amount calculating section 172b. The injection rate of the physiological saline in the test injection is set to the same as the injection rate of the chemical liquid in the test injection, that is, the injection rate of the chemical liquid in the main injection calculated by first chemical liquid injection rate calculating section 171b. For the injection time of the physiological saline in the test injection, a predetermined time, for example 5 seconds, can be preset. Second chemical liquid injection amount calculating section 172b calculates the injection amount of the physiological saline in the test injection from the injection rate and the injection time obtained as described above. For the injection time of the physiological saline in the test injection, a predetermined value may be set as a default value and the operator may change the value as required.

When the injection time of the chemical liquid is preset in both the main injection and the test injection as described above, the operator is only required to input the weight of the patient as the data for determining the injection conditions for the chemical liquid.

As described above, control section 161 controls the overall operation of chemical liquid injector 100 in accordance with the operation by the operator. Although the operation of chemical liquid injector 100 includes general operations performed in a typical chemical liquid injector, the operation particularly relating to the present invention includes controlling the operation of piston driving mechanism 130 in accordance with the selected injection mode and the injection conditions determined by injection condition determining section 170 and displaying the required information on display device 163. Each of the two injection modes to be performed is input selectively from input device 162. When the test injection association mode is selected, control section 161 controls the operation of piston driving mechanism 130 such that a preset injection suspension time is interposed between the test injection and the main injection. The injection suspension time may be a time period necessary for preparation of the patient for the main scan such as holding his breath, and specifically, may be approximately five to seven seconds.

Control section 141 transmits an injection start signal for the chemical liquid to X-ray CT apparatus 300 through interface 147 simultaneously with the start of the test injection.

As described above, X-ray CT apparatus 300 has imaging unit 301 and imaging control unit 302 as described above.

Imaging unit 301 has an X-ray source which applies X-rays to the patient and a data collecting section which collects data of X-ray projection transmitted through the patient. Imaging control unit 302 has an image data producing section, a scan control section, a display device, and an input device.

The image data producing section reconstructs the X-ray projection data collected by the data collecting section to produce CT image data. The display device displays, as required, the CT image data produced by the image data producing section, a graph showing changes in CT value over time measured from the CT image data in real time, the operational state of CT apparatus 300, imaging conditions and the like. The input device is used to input the imaging conditions and the like.

The scan control section generally controls the X-ray source, the data collecting section, the image data producing section, and the display section. The scan control section also measures the CT value from the CT image data produced by the image data producing section in bolus tracking and causes the X-ray source to perform the main scan based on the manner of changes in CT value over time, as later described in detail. The scan control section also functions as an interface with chemical liquid injector 100.

Next, the operation of the X-ray CT system according to the present embodiment is described.

First, the operator mounts, on injection head 110, syringes 200C and 200P each filled with the chemical liquid to be injected into the patient. Alternatively, the operator mounts empty syringes 200C and 200P filled with no chemical liquid on injection head 110 and then connects a predetermined chemical liquid container (not shown) to each of syringes 200C and 200P with a conventionally appropriate method. In this state, pistons 222 of syringes 200C and 200P are individually moved rearward to fill the predetermined chemical liquid into syringe assembly 200, so that each of syringes 200C and 200P mounted on the injection head may be filled with the chemical liquid.

The types of syringe 200 in terms of the filling of the chemical liquid include the syringe previously filled with the chemical liquid (pre-filled syringe) and the syringe filled with the chemical liquid onsite where it is used, as described above, and both of them can be used in the present invention. In the pre-filled syringe, before or after the mounting of syringes 200C and 200P on injection head 110, the injection needle or the catheter is connected to syringes 200C and 200P through extension tube 230.

A syringe to which an RFID tag having various data recorded thereon is attached can be used in the present invention. In this case, preferably, injection head 110 includes a reader/writer which reads the data from the RFID tag on mounted syringe assembly 200 such that the mounting of syringes 200C and 200P allows the reading of the data recorded on the RFID tag or the rewriting of the data. In this case, the iodine concentration of the chemical liquid may be recorded as one data on the RFID tag of syringe 200C filled with the chemical liquid, and the iodine concentration may be read by the reader/writer and used in the calculation of the injection amount of the chemical liquid in the main injection by first chemical liquid injection amount calculating section 171a.

Once the operator checks that syringes 200C and 200P are mounted on the injection head and that the injection needle or the catheter is connected to syringes 200C and 200P through extension tube 230, the operator performs a predetermined input operation indicating that the checking is completed through input device 162.

In response to the input operation, control section 161 performs an initialization operation for piston driving mechanism 130. The initialization operation includes driving both piston driving mechanisms 130 to move piston holding mechanism 133 forward and causing piston holding mechanisms 133 to hold pistons 222 of syringes 200C and 200P.

After the initialization operation for piston driving mechanism 130, control section 161 releases air from extension tube 230 or the like based on a predetermined operation performed by the operator. The air removal includes simultaneously driving both piston driving mechanisms 130 to move piston holding mechanisms 133 forward further to push the chemical liquid in syringes 200C and 200P, thereby filling the chemical liquid into extension tube 230 connected to syringes 200C and 200P and the injection needle or the catheter connected to extension tube 230. The simultaneous driving of both piston driving mechanisms 130 to remove air from both syringes 200C and 200P simultaneously in this manner can prevent air pushed out of one of the syringes from flowing into the other syringe. Since the moving amount of piston holding mechanism 133 required for the air removal depends on the length of extension tube 230 and the like, the moving amount of piston holding mechanism 133 for the air removal can be preferably set arbitrarily in order to avoid wasting the chemical liquid.

To allow a check of whether or not the air is sufficiently removed through the air removal, the chemical liquid injector preferably includes a bubble sensor (not shown) which detects bubbles present in extension tube 230 and the like. The bubble sensor can be provided by using a known sensor usable for detecting the bubbles in the tube such as an ultrasonic sensor, an optical sensor, and a capacitance sensor. The bubble detection with bubble sensor can be performed not only during the air removal but also during the chemical liquid injection operation. When the bubble sensor is used, an alarm can be issued to the operator through a lamp or a sound, or the operation of piston driving mechanism 130 can be stopped in response to the detection of bubbles, so that the chemical liquid containing the bubbles mixed therein can be prevented from being injected into the patient.

In the system in which the chemical liquid is filled into each of syringes 200C and 200P from the chemical liquid container and the filled chemical liquid is injected into the patient as described above, a liquid-level sensor (not shown) which detects the liquid level in the chemical liquid container is preferably provided to allow the detection of the presence or absence of the chemical liquid in the chemical liquid container. In this case, an alarm can be issued to the operator, or the operation of filling the chemical liquid can be stopped on the basis of the detection result of the liquid-level sensor, thereby preventing the air from being sucked into syringes 200C and 200P.

After the air removal is finished, the operator places or inserts the injection needle or the catheter connected to the leading end of extension tube 230 into a blood vessel of the patient. Through those steps, the preparation for injecting the chemical liquid filled in each of syringes 200C and 200P into the patient is completed.

Next, control section 161 displays a screen for setting injection conditions on display device 163. Description is made herein with an example in which display device 163 is a touch panel and also serves as input device 162. Thus, in the following description, display device 163 and input device 162 may be referred to as the touch panel.

Figure 5:
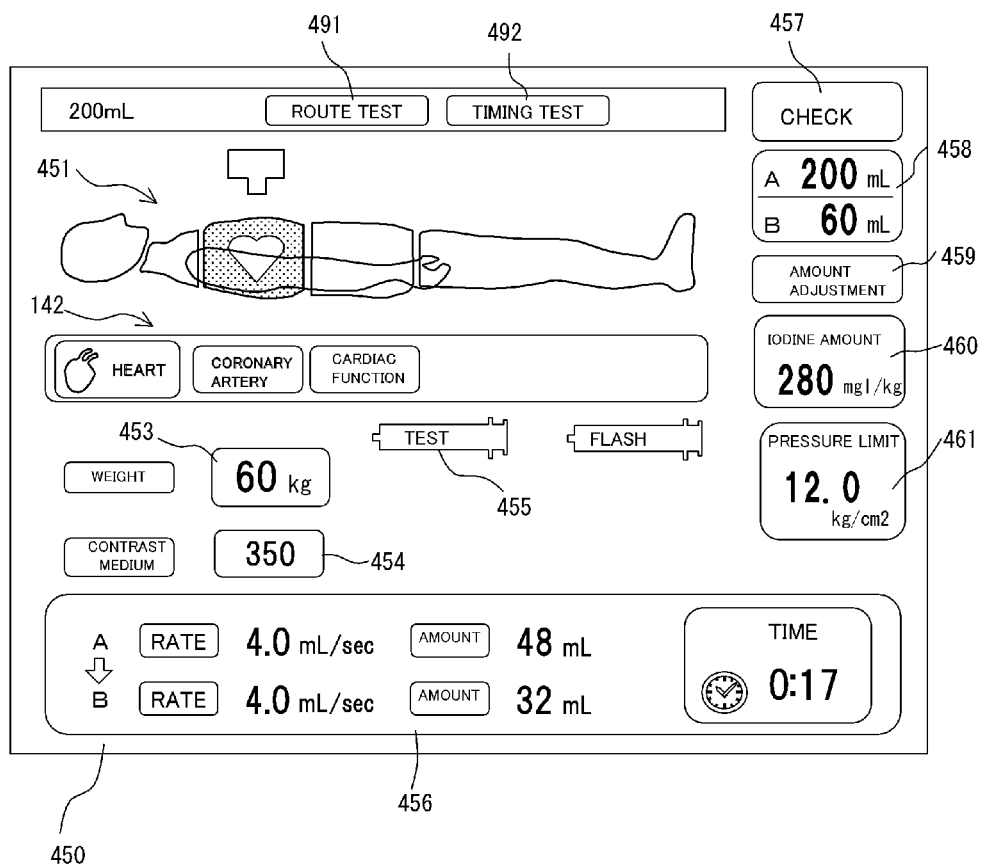
FIG. 5 A diagram showing an example of a screen for setting injection conditions displayed on a display device.

FIG. 5 shows an example of the screen for setting injection conditions displayed on display device 153. Setting screen 450 shown in FIG. 5 displays body part selecting buttons 451, imaging region selecting buttons 452, weight setting button 453, test injection association mode selecting button 455, main injection condition display window 456, check button 457 and the like. In FIG. 5, characters "A" and "B" representing the syringes show syringe 200C filled with the contrast medium and syringe 200P filled with the physiological saline, respectively. This also applies to FIG. 6 and FIG. 7 described later.

Body part selecting buttons 451 have a plurality of buttons provided by dividing an image representing a lying patient into a head part, a neck part, a chest part, a abdomen part, and a leg portion, for example. When the operator selects and touches one of them, the part corresponding to the touched button is input. The selected button is displayed to allow a visual distinction from the other body parts. FIG. 5 shows the state in which the chest portion is selected.

Imaging region selecting buttons 452 have one or more buttons displayed in response to the input of the body part and specifically showing imaging regions of the selected body part. The operator selects and touches the button representing the imaging region of interest to input the imaging region corresponding to the touched region. FIG. 5 shows the state in which the heart is selected as the imaging region, and the coronary artery is selected in the heart.

Weight setting button 453 is a button for inputting the weight of the patient. Test injection association mode selecting button 455 is a button touched in selecting the test injection association mode. When the test injection association mode is selected, the change of the color of test injection association mode selecting button 455 or the like is performed so that the selection of that mode can be visually recognized by the operator.

Iodine concentration display window 454 displays the iodine concentration of the contrast medium filled in syringe 200C. Syringe capacity display window 458 displays the capacities of mounted syringes 200C and 200P. Iodine amount display window 460 displays the iodine amount required per kilogram of the weight of the patient. Pressure limit display window 461 displays the pressure limit value of mounted syringes 200C and 200P. The values displayed in these display windows are preset as default values together with the injection times of the contrast medium and the physiological saline, and these values can be changed as appropriate by the operator through the operation of amount adjustment button 459.

Main injection condition display window 456 displays the injection conditions in the main injection determined by main injection condition determining section 171 of injection condition determining section 170. Specifically, in the present embodiment, the injection rate and the injection amount of the contrast medium, the injection rate and the injection amount of the physiological saline, and the injection time of the contrast medium including the injection suspension time are displayed in main injection condition display window 456.

The operator touches necessary buttons of body part selecting buttons 451 and imaging region selecting buttons 452 to select the imaging region. In addition, the operator inputs the weight with weight determining button 453, and changes the injection time or the like as required. Once the data is input, injection condition determining section 170 calculates the injection rates and the injection amounts of the contrast medium and the physiological saline in the main injection and the test injection based on the input data.

The calculated values are transmitted to control section 161 which then creates an injection protocol in accordance with the injection conditions determined by injection condition determining section 170. In the creation of the injection protocol, control section 161 takes account of whether or not the test injection association mode is selected. When the test injection association mode is not selected, control section 161 creates the injection protocol for the main injection. When the test injection association mode is selected, control section 161 creates the injection protocol for the test injection and the main injection between which the preset injection suspension time is interposed.

When the operator touches check button 457 after the input of the necessary data, control section 161 displays a check screen for allowing the operator to check the created injection protocol on display device 163.

Figure 6:
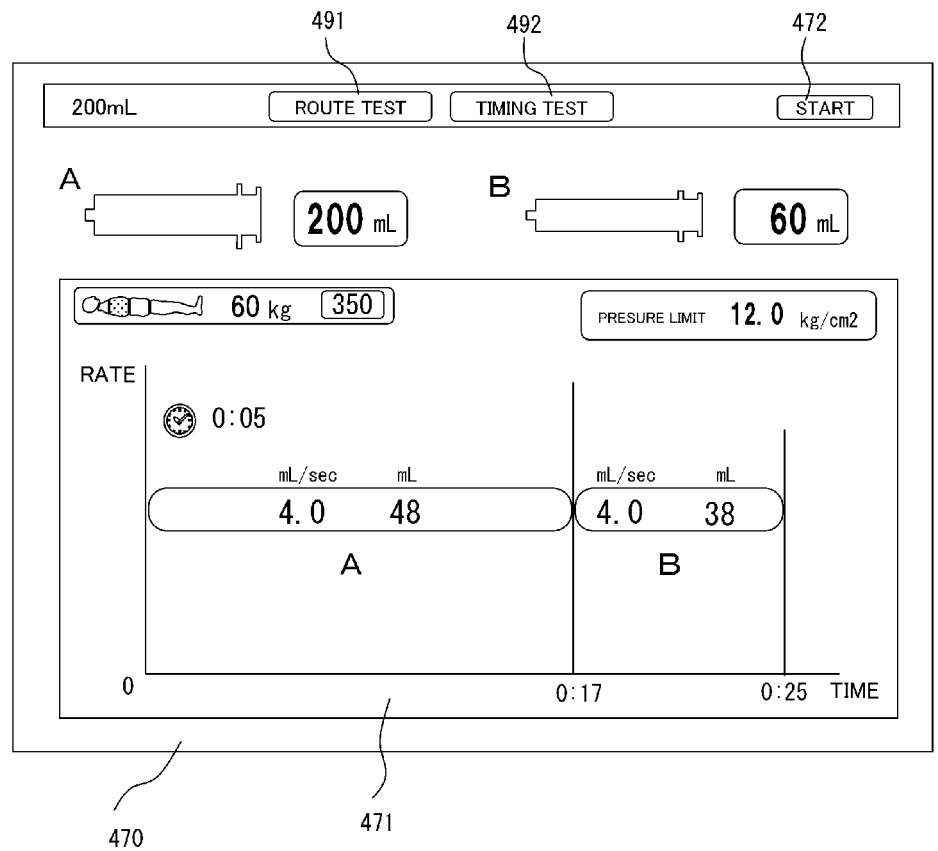
FIG. 6 A diagram showing an example of a screen for checking injection conditions when a test injection association mode is not selected, displayed on the display device.

FIG. 6 shows check screen 470 displayed when the test injection association mode is not selected, that is, when the chemical liquid injection should be performed in the standard mode. Check screen 470 includes injection graph 471. Injection graph 471 enables the operator to understand the injection protocol intuitively. In the example of injection graph 471 shown in FIG. 6, the horizontal axis represents the injection time (sec) and the vertical axis represents the injection rate (mL/sec). The graph shows that 48 mL of the contrast medium (represented by A in the graph) is injected at an injection rate of 4.0 mL/sec for 12 seconds, and subsequently, 38 mL of the physiological saline (represented by B in the graph) is injected at an injection rate of 4.0 mL/sec for 8 seconds. The injection time of the contrast medium includes an interruption time of 5 seconds immediately after the start, and the contrast medium is injected after the elapse of the interruption time, so that the contrast medium is actually injected for 12 seconds.

The operator checks check screen 470, and touches start button 472 if the displayed items present no problem. Then, control section 161 controls the operation of piston driving mechanism 130 such that the main injection is performed in accordance with the created injection protocol.

Alternatively, when the test injection association mode is selected on setting screen 450 shown in FIG. 5, control section 161 displays the injection protocol for a series of operations including the test injection on display device 163.

Figure 7:
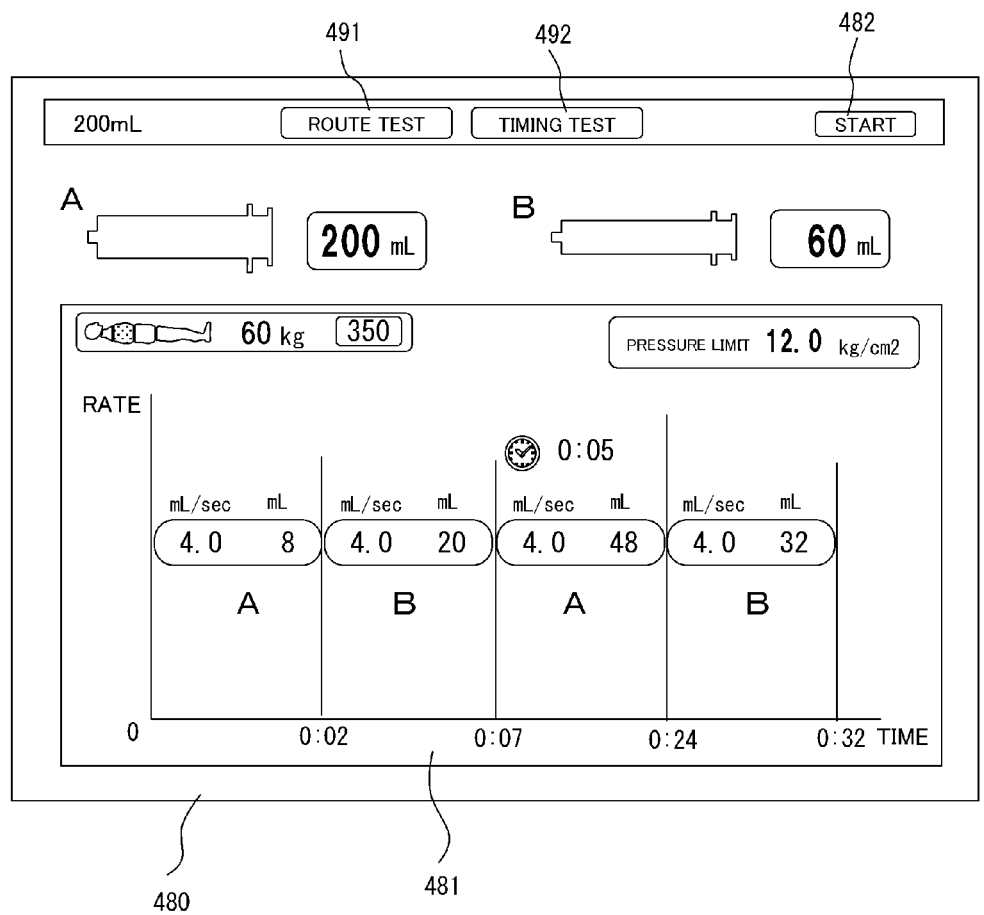
FIG. 7 A diagram showing an example of the screen for checking injection conditions when the test injection association mode is selected, displayed on the display device.

FIG. 7 shows check screen 480 displayed when the test injection association mode is selected. Similarly to FIG. 6, check screen 480 includes injection graph 481 for allowing the operator to understand the injection protocol intuitively. In the example of injection graph 481 shown in FIG. 7, the horizontal axis represents the injection time (sec) and the vertical axis represents the injection rate (mL/sec). The graph shows that test injection is performed for 7 seconds, then the injection suspension time of 5 seconds is inserted, and subsequently, the main injection is performed. More particularly, in the test injection, 8 mL of the contrast medium is injected at an injection rate of 4.0 mL/sec for 2 seconds, and immediately following, 20 mL of the physiological saline is injected at an injection rate of 4.0 mL/sec for 5 seconds. In the main injection, after the above injection suspension time, 48 mL of the contrast medium is injected at an injection rate of 4.0 mL/sec for 12 seconds, and immediately following, 32 mL of the physiological saline is injected at an injection rate of 4.0 mL/sec for 8 seconds.

In the conventional test injection method, the setting of the injection conditions is performed independently for each of the test injection and the main injection, and the check screens for those injections are displayed individually. In the present embodiment, however, check screen 480 in the test injection association mode displays the injection conditions for the test injection and the injection conditions for the main injection on the one screen as shown in FIG. 7 to allow the easy understanding of those injection conditions.

X-ray CT apparatus 300 performs the bolus tracking associated with the test injection and the main scan associated with the main injection, and the predetermined scan suspension time is set between the bolus tracking and the main scan. During the scan suspension time, a notification is provided for the patient to ask him to hold his breath. The scan suspension time includes the time interval from the holding of the patient's breath to the stabilization of the heart rate at a relatively low level. Thus, the total time of the injection time of the physiological saline in the test injection and the subsequent injection suspension time is set such that the time interval from the start of the injection of the physiological saline in the test injection to the start of the injection of the contrast medium in the main injection, which corresponds to the time interval in which the contrast medium is not injected between the test injection and the main injection, is equal to or longer than the total amount of the time (approximately 5 seconds) required for the notification to ask the patient to hold his breath and the time (approximately 5 seconds) taken for the stabilization of the heart rate of the patient. In the present embodiment, the total of the injection time of the physiological saline and the subsequent injection suspension time is 10 seconds as described above.

The operator checks check screen 480, and touches start button 482 when the displayed items present no problem. Then, control section 161 controls the operation of piston driving mechanism 130 such that the test injection and the main injection based on the created injection protocol are performed in a series of operations including the injection suspension time interposed therebetween.

Simultaneously with the start of the test injection, control section 161 transmits a start signal for the test injection to X-ray CT apparatus 300 through interface 147. Upon reception of the start signal, X-ray CT apparatus 300 causes imaging control unit 301 to apply X-rays to the patient to perform the bolus tracking. The bolus tracking includes monitoring the CT value at regular time intervals. Since the time taken from the injection of the contrast medium to the arrival thereof at the coronary artery is typically assumed to be approximately 20 seconds in imaging the coronary artery, the start time of the bolus tracking is set to a point before the arrival time. In the present embodiment, the start time of the bolus tracking is set to 8 seconds after the injection start of the contrast medium in the test injection, and the scan interval in the bolus tracking is set to 1 second.

Imaging control unit 302 of X-ray CT apparatus 300 monitors the CT value in the bolus tracking, and uses a point immediately after the CT value exceeding the peak value as a trigger to cause imaging unit 301 to start the main scan. In the following, the operation of X-ray CT apparatus 300 is described with reference to FIG. 8.

Figure 8:
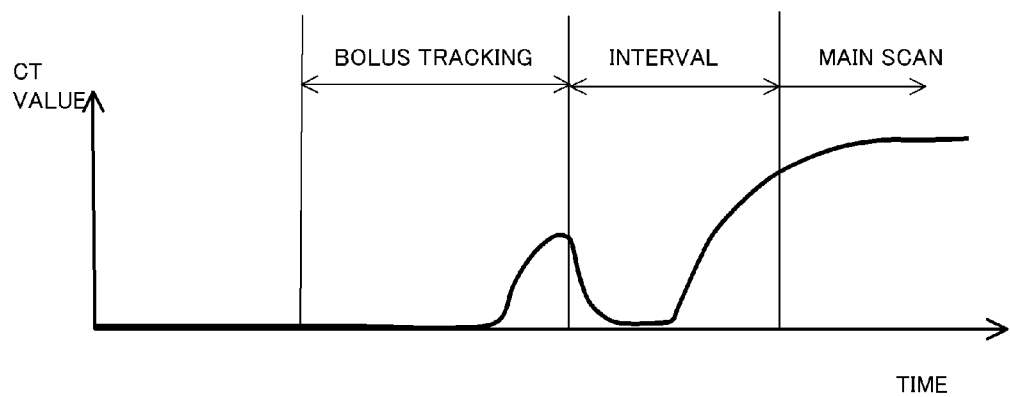
FIG. 8 A graph showing an example of a curve representing changes in CT value over time when a contrast medium and physiological saline are injected in the test injection association mode.

FIG. 8 is a graph showing a curve representing changes in the CT value over time when the test injection and the main injection are performed according to the present embodiment. As shown in FIG. 8, the CT value starts to increase after the elapse of a certain time since the start of the test injection. A small amount of the contrast medium is injected in the test injection for a shorter time period than in the main injection, so that the CT value reaches the peak several seconds after it starts to increase, and then reduces.

X-ray CT apparatus 300 stops the bolus tracking immediately after the CT value passes the peak, and starts the scan suspension time. The start timing of the scan suspension time is set to the point immediately after the CT value passes the peak because, although the most characteristic point on the curve representing the changes in the CT value is the peak of the CT value, the determination of whether or not the CT value reaches the peak is made from the comparison with the previous measurement results and only the point after the value passes the peak can be determined in real time. If a specific point on the curve representing the changes in the CT value can be determined in real time, a point other than the point immediately after the value passes the peak may be set as the trigger.

During the scan suspension time, the CT again starts to increase since the contrast medium injected for the main injection arrives. To avoid interference between the changes in the CT value caused by the test injection and the changes in the CT value caused by the main injection, it is important that the increase in the CT value resulting from the main injection should be started after the CT value resulting from the test injection sufficiently reduces.

During the scan suspension time, the notification is provided for the patient to ask him to hold his breath, and the patient holds his breath in response to the notification. The main scan is desirably started after the patient holds his breath and his heart rate stabilizes at a relatively low level. Thus, the scan suspension time between the bolus tracking and the main scan is set in view of the time required for the notification to ask the patient to hold his breath, the time to stabilize the heart rate of the patient, and an additional delay time additionally set from the peak on the CT value curve for the trigger to the start timing of the main scan when the CT value curve for the trigger is regarded as the CT value curve for the main scan, similarly to the test injection method. In the present embodiment, these times are set to 5 seconds each, and 15 seconds are set in total for the scan suspension time.

X-ray CT apparatus 300 starts the main scan after the above scan suspension time.

As described above, in the present embodiment, the test injection and the main injection of the contrast medium are performed as a series operation including the injection suspension time interposed therebetween, and the main scan performed by X-ray CT apparatus 300 is started after the predetermined scan suspension time associated with the injection suspension time between the test injection and the main injection by using the point immediately after the CT value passes the peak resulting from the test injection as the trigger. The main scan is started such that the peak of the CT value measured by imaging control unit 302 is used as the trigger, and the presence of the peak of the CT value results from the injection suspension time interposed between the test injection and the main injection performed by chemical liquid injector 100, and the manner of changes in the CT value in the series of injection operations results from variations among individuals such as the circulating blood volume, the cardiac output, the vascular resistance of the patient and the like. Since the main scan is performed by using the peak of the CT value as the trigger, the appropriate imaging timing depending on the variations among individuals can be obtained similarly to the test injection method, although the imaging technique similar to the bolus tracking method is employed. This can improve the test throughput as compared with the test injection method, and the parameters for determining the imaging timing in the conventionally performed test injection method can be used as they are.

In addition, since the test injection and the main injection are performed as a series operation including the injection suspension time interposed therebetween, the hemodynamic variations between the test injection and the main injection are smaller than that in the test injection method. This allows the imaging in a better timing to achieve the stable imaging effect. Furthermore, the bolus tracking can be performed at a position where the timing needs to be provided even in a region with faster flowback, so that the present invention can be applied to regions in which the timing is difficult to provide conventionally.

Since the setting of the injection suspension time between the test injection and the main injection prevents a trade-off between the time from the start of the contrast medium injection to the time of the start of the main scan and the use amount of the contrast medium as in the bolus tracking method, the main injection can be performed only during the injection time required for the main scan imaging. As a result, the use amount of the contrast medium can be reduced as compared with the bolus tracking method, although the technique similar to the bolus tracking is used. The injection suspension time can be freely set in view of the times taken to make the notification to hold the patient's breath and to stabilize the heart rate.

When attention is paid on chemical liquid injector 100, chemical liquid injector 100 performs the test injection and the main injection by presetting the injection times of the contrast medium and the physiological saline in the test injection and the main injection, calculating the injection amount of the contrast medium in the main injection based on the weight of the patient, and determining, from the calculated injection amount of the contrast medium and each of the preset injection times, the injection rate of the contrast medium in the main injection, the injection amount and the injection rate of the contrast medium in the test injection, and the injection amount and the injection rate of the physiological saline in the test injection. More particularly, chemical liquid injector 100 calculates the injection rate of the contrast medium in the main injection from the calculated injection amount of the contrast medium and the preset injection time, sets the injection rate of the physiological saline in the main injection, the injection rate of the contrast medium in the test injection, and the injection rate of the physiological saline in the test injection to the same as the calculated injection rate of the contrast medium in the main injection, and calculates the injection amount of the physiological saline in the main injection, and the injection amounts of the contrast medium and the physiological saline in the test injection from the injection rate, the preset injection time of the physiological saline in the main injection, and the injection times of the contrast medium and the physiological saline in the test injection.

The determination of the injection conditions for the chemical liquid as described above can realize the simple input operation without requiring performing data input for each time even when the test injection and the main injection are performed. The presetting of the injection time of the chemical liquid or the like can determine the injection conditions for the chemical liquid in the test injection and the main injection at least from the weight of the patient to simplify the data input operation extremely.

Although only the main injection is performed in the present embodiment when the test injection association mode is not selected, the test injection may be performed independently of the main injection similarly to the conventional case. Thus, as shown in FIG. 5, setting screen 460 displays timing test button 492, and when the operator touches button 492, the display of the touch panel is switched to a screen for the test injection (not shown). The operator can perform predetermined setting for the test injection on the displayed screen to cause chemical liquid injector 100 to perform the test injection.

Setting screen 450 also displays patency route test button 491. The operator touches button 491 to allow chemical liquid injector 100 to perform a patency route test. The route test refers to a test for checking whether or not the chemical liquid flow path from the syringe to the patient is normally ensured. In general, the route test includes detecting the pressure applied to the syringe filled with the chemical liquid (specifically, the physiological saline) while the chemical liquid is injected into the patient, and when the detected pressure falls within a preset predetermined range, it is determined that the chemical liquid flow path is normally ensured. Alternatively, when the pressure is lower than the predetermined range, a liquid leak from the chemical liquid flow path is expected. In contrast, when the pressure is higher than the range, clogging in the chemical liquid flowing path is expected.

Since the test injection and the main injection are performed in the series of operations in the test injection association mode in the above embodiment, replacement of syringe 200C or 200P cannot be performed substantially between the test injection and the main injection. In some syringes to be mounted on injection head 110, the total injection amount equal to the total of the calculated injection amount of the chemical liquid in the test injection and the injection amount in the main injection may exceed the capacity of the mounted syringe. In this case, the chemical liquid may be exhausted before the completion of the injection and the intended diagnostic image may not be obtained.

In the present embodiment, when the test injection association mode is selected and the calculated total injection amount of the chemical liquid exceeds the capacity of the syringe, the numeric value representing the amount of the chemical liquid of interest displayed in main injection condition display window 456 flashes on setting screen 450 shown in FIG. 5 to call the attention of the operator. When the display is flashing in this manner, the operator can change the injection conditions for the chemical liquid in the main injection as appropriate such that the total injection amount of the chemical liquid determined by injection condition determining section 170 does not exceed the amount of the chemical liquid filled in each of syringes 200C and 200P. This change can be performed by the operator touching amount adjustment button 459 (see FIG. 5) to switch to an amount adjustment mode in which the injection time or the like is changed.

The present invention has been described in detail with reference to the representative embodiment. The present invention is not limited to the embodiment described above, and various modifications can be made.

For example, in the above embodiment, chemical liquid injector 100 is connected to X-ray CT apparatus 300, and the signal for starting the injection is transmitted to X-ray CT apparatus 300. However, chemical liquid injector 100 may not be connected to X-ray CT apparatus 300, and in this case, the operator performs a predetermined operation on X-ray CT apparatus 300 after the start of the test injection to cause X-ray CT apparatus 300 to perform the bolus tracking.

The above embodiment shows the example in which X-ray CT apparatus 300 determines the trigger of the transition from the bolus tracking to the main scan after the scan suspension time. Alternatively, the curve representing the changes in the CT value shown in FIG. 8 may be displayed in real time on a display device (not shown) of X-ray CT apparatus 300, the operator may visually determine the peak of the CT value, and may perform a predetermined operation to cause X-ray CT apparatus 300 to perform the main scan immediately after the peak is passed. In this case, X-ray CT apparatus 300 performs the main scan following the scan suspension time after the operation performed by the operator.

Although the above embodiment has shown the example in which two chemical liquid syringes 200C and 200P are mounted on injection head 110, the number of the chemical liquid syringes mountable on injection head 110 may be one or three or more. In this case, the numbers of recess portions 114, piston driving mechanisms 130 and the like provided are equal to the number of the mounted chemical liquid syringes. The size of the chemical liquid syringe mountable on injection head 110 is arbitrarily determined. The size of recess portion 114, the stroke of rod 131 and the like are set to adapt to the size of the chemical liquid syringe to be mounted. When a plurality of chemical liquid syringes is mounted, the chemical liquid syringes may have different sizes.

Although the above embodiment has shown the injection order in which the contrast medium is injected and then the physiological saline is injected in the main injection of the chemical liquid, the injection order of the chemical liquids in the main injection is not limited thereto, and various injection orders can be employed as described below, for example.

(1) contrast medium→(contrast medium+physiological saline)

(2) contrast medium→(contrast medium+physiological saline)→physiological saline (3) contrast medium→(contrast medium/physiological saline)

(4) contrast medium→(contrast medium/physiological saline)→physiological saline

In (1), after the injection of a predetermined amount of the contrast medium, a mixture of the contrast medium and the physiological saline is injected. In (2), the physiological saline is further injected after the injection in (1). In (3), the contrast medium is first injected at 100%, and then, the amount of the physiological saline is gradually increased to reduce the proportion of the contrast medium. In (4), the proportion of the contrast medium is further reduced in (3), and finally, only the physiological saline is injected.

These injection orders can be selected as appropriate based on the imaging region of interest, the diagnosis purpose and the like. Injection condition determining section 170 determines the injection conditions for the contrast medium and the physiological saline in accordance with the injection order. In any case, the main injection is performed following the injection suspension time after the test injection.

The mixture injection of the contrast medium and the physiological saline can also be used in the test injection. For example, after a mixture of the contrast medium and the physiological saline is injected in the test injection, only the physiological saline can be injected to push the contrast medium. Even when the contrast medium is diluted before injection, the CT value increases in substantially the same manner as when it is not diluted. The injection of the contrast medium diluted with the physiological saline in the test injection can reduce the injection amount of the contrast medium in the test injection to ease a physical burden on the patient. The concentration of the contrast medium in this case is arbitrarily set in the range in which the manner of increase in the CT value is not affected.

In the above embodiment, the weight of the patient is used as the parameter, the injection conditions for the chemical liquid are determined from the relationship between the required iodine amount and the iodine concentration of the contrast medium used, and the injection time of the chemical liquid is basically the preset time. To determine the injection conditions, however, the parameters may include not only the weight of the patient but also the sex, height, body surface area of the patient, and a combination thereof. The required iodine amount, the injection time of the chemical liquid and the like may be preferably changed in accordance with the physical factor of the patient, the factor associated with X-ray CT apparatus 300 and the like. In the following, description is made of the correction of the injection conditions for the chemical liquid in association with these factors.

<Cardiac Output of Patient>

When the contrast medium is injected into a patient having a cardiac output higher than normal such as a patient with valvular disease, the concentration of the contrast medium in blood may be reduced before the contrast medium reaches the imaging region of interest to fail to obtain a desired image. In this case, the contrast medium is preferably injected so as to give an iodine amount larger than normal.

To obtain a desired image in such a patient having a cardiac output higher than normal, the chemical liquid injection system may further include a cardiac output flowmeter for measuring the cardiac output of the patient to allow the measurement of the cardiac output of the patient prior to the determination of the injection conditions for the chemical liquid, and chemical liquid injector 100 may be formed such that first chemical liquid injection amount calculating section 171a of main injection condition determining section 171 calculates the injection amount of the contrast medium corrected by taking account of the measurement value of the cardiac output.

The correction of the injection amount of the contrast medium in first chemical liquid calculating section 171a changes the injection rate of the contrast medium calculated by first chemical liquid injection rate calculating section 171b of main injection condition determining section 171 and the injection amount of the physiological saline calculated by second chemical liquid injection amount calculating section 171c. In addition, in test injection condition determining section 172, the injection amount of the contrast medium calculated by first chemical liquid injection amount calculating section 172a and the injection amount of the physiological saline calculated by second chemical liquid injection amount calculating section 172b are changed.

In the correction of the injection amount of the contrast medium in the main injection in view of the measurement value of the cardiac output of the patient, when the measured cardiac output is higher than normal in (1) described above, the value of the required iodine amount I is increased in accordance with the measurement value of the cardiac output. In contrast, when the measured cardiac output is lower than normal, the value of the required iodine amount I is set to be lower in accordance with the measurement value of the cardiac output. Thus, the value of the required iodine amount I can be set manually by the operator in accordance with the measurement value of the cardiac output. Alternatively, when the cardiac output flowmeter is connected to chemical liquid injector 100 to allow data transmission to chemical liquid injector 100, first chemical liquid injection amount calculating section 171a of main injection condition determining section 171 can increase or reduce the value of the required iodine amount I based on the data transmitted from the cardiac output flowmeter.

<Effective Energy of X-Ray CT Apparatus>

Since less X-rays pass a patient having more fat than normal, imaging of such a patient may be performed at a tube voltage of X-ray CT apparatus 300 higher than normal in order to provide favorable images. The increased tube voltage enhances the effective energy. Depending on the type of X-ray CT apparatus 300, the effective energy may vary even at the same tube voltage. The CT value depends on the effective energy of the X-rays of X-ray CT apparatus 300, and the CT value is reduced as the effective energy is increased. To obtain a desired CT value when the high effective energy is used for imaging, the injection amount of the contrast medium may be increased than normal.

To provide a desired CT value even when the patient having much fat is imaged or when X-ray CT apparatus 300 is changed, chemical liquid injector 100 may be formed such that first chemical liquid injection amount calculating section 171a of main injection condition determining section 171 calculates the injection amount of the contrast medium corrected in view of the effective energy of X-ray CT apparatus 300.

In the correction of the injection conditions for the chemical liquid in view of the effective energy of X-ray CT apparatus 300, when the effective energy of X-ray CT apparatus 300 is higher than normal in the expression (1) described above, the value of the required iodine amount I is set to be larger in accordance with the value of the effective energy. In contrast, when the effective energy is lower than normal, the value of the required iodine amount I is set to be lower in accordance with the value of the effective energy. To achieve this, the value of the required iodine amount I can be set manually by the operator in accordance with the value of the effective energy of X-ray CT apparatus 300. Alternatively, when X-ray CT apparatus 300 is connected to chemical liquid injector 100 to allow data transmission to chemical liquid injector 100, first chemical liquid injection amount calculating section 171a of main injection condition determining section 171 can increase or reduce the value of the required iodine amount I based on the data transmitted from X-ray CT apparatus 300.

<Results of Bolus tracking>

In the bolus tracking, the manner of increase in the CT value in the test injection can be observed. The injection rate of the contrast medium in the main injection may be changed in accordance with the results of the bolus tracking in order to provide the more favorable visualization effect in the main injection.

For example, when the peak value of the CT value obtained in the bolus tracking is lower than a value expected when the contrast medium is injected under the set test injection conditions, the injection rate of the contrast medium in the main injection is corrected to an injection rate higher than the injection rate calculated by first chemical liquid injection rate calculating section 171b before the injection of the contrast medium. This increases the CT value in the main injection easily as compared with the CT value in the test injection. In contrast, when the peak value of the CT value obtained in the bolus tracking is higher than the expected value, the injection rate of the contrast medium in the main injection is corrected to an injection rate lower than the calculated injection rate before the injection of the contrast medium so that the CT value does not increase significantly.

The correction of the injection rate of the contrast medium in the main injection in accordance with the results of the bolus tracking as described above allows more favorable tomographic images of the patient to be obtained in association with variations among individuals. When the injection rate of the contrast medium is corrected, the other injection conditions such as the injection amount and the injection time are influenced. However, in view of the physical burden on the patient and the cost of the contrast medium, the injection amount of the contrast medium is not increased preferably. For this reason, the injection time is preferably shortened when the injection rate of the contrast medium is increased, for example.

Preferably, the correction of the injection rate is performed over the entire time interval of the main injection, that is, the main injection is performed at the corrected injection rate. Alternatively, the contrast medium may be injected at the injection rate calculated by first chemical liquid injection rate calculating section 171b at first, and the contrast medium may be injected at the corrected injection rate from a certain point in the main injection.

DESCRIPTION OF REFERENCE NUMERALS

100 CHEMICAL LIQUID INJECTOR
101 INJECTION CONTROL UNIT
110 INJECTION HEAD
130 PISTON DRIVING MECHANISM
161 CONTROL SECTION
162 INPUT DEVICE
163 DISPLAY DEVICE
170 INJECTION CONDITION DETERMINING SECTION
171 MAIN INJECTION CONDITION DETERMINING SECTION
171a FIRST CHEMICAL LIQUID INJECTION AMOUNT CALCULATING SECTION
171b FIRST CHEMICAL LIQUID INJECTION RATE CALCULATING SECTION
171c SECOND CHEMICAL LIQUID INJECTION AMOUNT CALCULATING SECTION
172 TEST INJECTION CONDITION DETERMINING SECTION
172a FIRST CHEMICAL LIQUID INJECTION AMOUNT CALCULATING SECTION
172b SECOND CHEMICAL LIQUID INJECTION AMOUNT CALCULATING SECTION
300 X-RAY CT APPARATUS
301 IMAGING UNIT
302 IMAGING CONTROL UNIT

The invention claimed is:
1. A chemical liquid injector on which at least one syringe having a cylinder and a piston is mounted, the chemical liquid injector injecting a chemical liquid in the syringe by moving the piston of the mounted syringe forward, comprising:

a plurality of piston driving mechanisms driven individually so as to inject a contrast medium and a physiological saline as the chemical liquid by moving the piston of the mounted syringe forward;

a main injection condition determining section determining an injection condition for the chemical liquid in main injection;

a test injection condition determining section determining an injection condition for the chemical liquid in test injection performed prior to the main injection, a smaller injection amount of the chemical liquid being injected in the test injection than an injection amount in the main injection; and a control section creating an injection protocol in accordance with the injection conditions determined by the test injection condition determining section and the main injection condition determining section such that the chemical liquid is injected in a series of operations in which the test injection is performed, then a preset injection suspension time is present, and subsequently the main injection is performed, and the control section further controls operation of the piston driving mechanisms such that the physiological saline is injected immediately after the injection of the contrast medium in the test-injection in accordance with the injection protocol, wherein the main injection condition determining section determines an injection rate of the contrast medium in the main injection, and the test injection condition determining section determines injection rates of the contrast medium and the physiological saline in the test injection such that they are same as the injection rate of the contrast medium in the main injection.

2. The chemical liquid injector according to claim 1, wherein the main injection condition determining section has a first chemical liquid injection amount calculating section calculating an injection amount of the contrast medium in the main injection based on a weight of a patient to be injected with the contrast medium, and a first chemical liquid injection rate calculating section calculating an injection rate of the contrast medium in the main injection from the injection amount of the contrast medium calculated by the first chemical liquid injection amount calculating section and a preset injection time, and the test injection condition determining section has a first chemical liquid injection amount calculating section calculating an injection amount of the contrast medium in the test injection from the injection rate calculated by the first chemical liquid injection rate determining section and a preset injection time.

3. The chemical liquid injector according to claim 2, wherein the main injection condition determining section further includes a second chemical liquid injection amount calculating section calculating an injection amount of the physiological saline in the main injection from the injection rate calculated by the first chemical liquid injection rate calculating section and a preset injection time, the test injection condition determining section further includes a second chemical liquid injection amount calculating section calculating an injection amount of the physiological saline in the test injection from the injection rate calculated by the first chemical liquid injection rate calculating section of the main injection condition determining section and a preset injection time, and the control section controls operation of the piston driving mechanisms such that the physiological saline is injected immediately after the injection of the contrast medium in accordance with the injection conditions determined by the test injection condition determining section and the main injection condition determining section in the test injection and the main injection.

4. The chemical liquid injector according to any claim 1, further comprising a display device, wherein the control section displays the injection protocol created in accordance with the injection conditions determined by the test injection condition determining section and the main injection condition determining section in one screen on the display device.

5. A CT apparatus used with the chemical liquid injector according to claim 1 to obtain a CT image of the patient, comprising:

an imaging unit applying an X ray to the patient and collecting data of projection of the X ray transmitted through the patient; and an imaging control unit controlling operation of the imaging unit, reconstructing the data of projection of the X ray collected by the imaging unit to produce CT image data, and measuring a CT value from the produced CT image data, wherein the imaging control unit monitors the CT value through bolus tracking, and causes the imaging unit to perform a main scan after a preset scan suspension time by using a point immediately after the CT value passes a peak value as a trigger.

6. The CT apparatus according to claim 5, wherein the scan suspension time is set in association with an injection suspension time in the chemical liquid injector.

7. A method for injecting a contrast medium and a physiological saline as a chemical liquid, said method comprising the steps of:

determining an injection condition for the chemical liquid in main injection, the injection condition including an injection rate of the contrast medium in the main injection;

determining an injection condition for the chemical liquid in test injection performed prior to the main injection, a smaller injection amount of the chemical liquid being injected in the test injection than an injection amount in the main injection, the injection condition including injection rates of the contrast medium and the physiological saline in the test injection in which the injection rates are the same as the injection rate of the contrast medium in the main injection;

creating an injection protocol in accordance with the injection condition and the main injection condition such that the chemical liquid is injected in a series of operations in which the test injection is performed, then a preset injection suspension time is present, and subsequently the main injection is performed; and injecting the contrast medium and the physiological saline such that the physiological saline is injected immediately after the injection of the contrast medium in the test-injection in accordance with the injection protocol.

8. The method according to claim 7, wherein the step of determining the injection condition in the main injection includes calculating an injection amount of the contrast medium in the main injection based on a weight of a patient to be injected with the contrast medium, and calculating an injection rate of the contrast medium in the main injection from the injection amount of the contrast medium an injection time, and the step of determining the injection condition in the test injection includes calculating an injection amount of the contrast medium in the test injection from the injection rate and an injection time.

9. The method according to claim 8, wherein the step of determining the injection condition in the main injection includes calculating an injection amount of the physiological saline in the main injection from the injection rate of the contrast medium an injection time, the step of determining the injection condition in the test injection includes calculating an injection amount of the physiological saline in the test injection from the injection rate of the contrast medium and an injection time, and the step of injecting includes injecting the physiological saline immediately after injection of the contrast medium in the test injection and the main injection.

10. A CT system comprising:

a CT apparatus including an imaging unit applying an X ray to the patient and collecting data of projection of the X ray transmitted through the patient and an imaging control unit controlling operation of the imaging unit, reconstructing the data of projection of the X ray collected by the imaging unit to produce CT image data, and measuring a CT value from the produced CT image data;

a chemical liquid injector including a plurality of piston driving mechanisms driven individually so as to inject a contrast medium and a physiological saline as the chemical liquid by moving the piston of the mounted syringe forward;

a main injection condition determining section determining an injection condition for the chemical liquid in main injection;

a test injection condition determining section determining an injection condition for the chemical liquid in test injection performed prior to the main injection, a smaller injection amount of the chemical liquid being injected in the test injection than an injection amount in the main injection; and a control section creating an injection protocol in accordance with the injection conditions determined by the test injection condition determining section and the main injection condition determining section such that the chemical liquid is injected in a series of operations in which the test injection is performed, then a preset injection suspension time is present, and subsequently the main injection is performed, and the control section further controls operation of the piston driving mechanisms such that the physiological saline is injected immediately after the injection of the contrast medium in the test-injection in accordance with the injection protocol, wherein the main injection condition determining section determines an injection rate of the contrast medium in the main injection, and the test injection condition determining section determines injection rates of the contrast medium and the physiological saline in the test injection such that they are same as the injection rate of the contrast medium in the main injection.

* * * * *